United States Patent [19]

Imokawa

[11] Patent Number: 5,258,548
[45] Date of Patent: Nov. 2, 1993

[54] METHOD FOR PREVENTING COLORATION OF AROMATIC ISOCYANATE COMPOUNDS

[75] Inventor: Toshiaki Imokawa, Niihama, Japan

[73] Assignee: Sumitomo Bayer Urethane Co., Ltd., Hyogo, Japan

[21] Appl. No.: 939,817

[22] Filed: Sep. 3, 1992

[30] Foreign Application Priority Data

Sep. 9, 1991 [JP] Japan .................................. 3-227898

[51] Int. Cl.$^5$ ........................................... C07C 263/18
[52] U.S. Cl. .................................... 560/333; 524/710; 560/331; 560/358; 560/359
[58] Field of Search ......................... 560/333; 524/710

[56] References Cited

U.S. PATENT DOCUMENTS

| | | | |
|---|---|---|---|
| 2,437,867 | 3/1948 | Verbanc | 560/333 |
| 2,957,903 | 10/1960 | Spiegler | 560/333 |
| 3,585,229 | 6/1971 | Christian et al. | 560/333 |
| 3,715,381 | 2/1973 | Spaunburgh et al. | 560/333 |
| 4,677,154 | 6/1987 | Narayan et al. | 524/710 |
| 4,724,247 | 2/1988 | Burton et al. | 524/128 |
| 5,175,349 | 12/1992 | Gupta et al. | 560/333 |

FOREIGN PATENT DOCUMENTS

| | | |
|---|---|---|
| 2930411 | 1/1981 | Fed. Rep. of Germany . |
| 57-82358 | 5/1982 | Japan . |
| 59-189116 | 10/1984 | Japan . |
| 1014043 | 12/1965 | United Kingdom . |

OTHER PUBLICATIONS

*Chemical Abstracts*, vol. 98, No. 3 Jan. 17, 1983, Abstract No. 16844n.
*Chemical Abstracts*, vol. 114, No. 26, Jul. 1, 1991, Abstract No. 248622r.
"*Polyurethane Resin*", p. 23, (1969), by Keiji Iwata.
*High Polymer*, vol. XVI, p. 214, (1967), by J. H. Saunders & K. C. Frisch.

*Primary Examiner*—José G. Dees
*Assistant Examiner*—Vera C. Clarke
*Attorney, Agent, or Firm*—Joseph C. Gil

[57] ABSTRACT

A method for preventing coloration of an aromatic isocyanate compound, which is characterized in that an organic phosphite ester of formula:

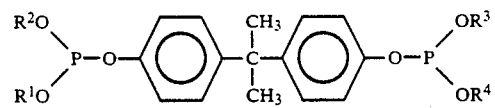

wherein $R^1$, $R^2$, $R^3$ and $R^4$ are, the same or different, each a $C_{4-20}$ hydrocarbon group, 2,6-di-tert.-butyl-4-methylphenol and triphenyl phosphite are added to the aromatic isocyanate compound.

1 Claim, No Drawings

METHOD FOR PREVENTING COLORATION OF AROMATIC ISOCYANATE COMPOUNDS

The present invention relates to a method for preventing aromatic isocyanate compounds from coloring owing to the air, light, heat and the like.

Aromatic isocyanate compounds such as diphenylmethane diisocyanate (referred to as MDI hereinafter) or toluene diisocyanate (referred to as TDI hereinafter) are so reactive that they are used as the raw materials for elastomers, foams, artificial leathers, spandexes, paints, adhesives, etc., by reacting them with active hydrogen compounds such as various polyols and amines having active hydrogens.

Although aromatic isocyanate compounds are colorless transparent or slightly pale-yellow immediately after being manufactured, they are colored when they are exposed to the air or light or heated during storage. Colored aromatic isocyanate compounds not only cannot be used as the raw materials for the artificial leathers, paints, etc., of white or pale-yellow color, but also are difficult to be used as the raw materials for elastomers, foams, etc.

Therefore, the compounds are purified, for example, by way of distillation under a well-controlled condition, and anti-oxidants or ultra-violet light absorbing agents etc. are further added to the compounds to prevent coloration during the storage.

To prevent coloration of the aromatic isocyanate compounds, addition of triallyl esters of phosphorous acid such as triphenyl phosphite (referred to as TPP hereinafter), trialkyl esters of phosphoric acid such as triethyl phosphate, organic phosphorus compounds such as 1,1,3-tris[2-methyl-4-di(tridecyloxy)phosphinoxy-5-tert.-butylphenyl]butane, epichlorohydrin, tetraphenyldipropylene glycol diphosphite, or anti-oxidants such as 2,6-di-tert.-butyl-4-methylphenol (abbreviated as BHT hereinafter), to the aromatic isocyanate compounds is described in U.S. Pat. No. 2,957,903, Japanese Patent Kokai Publication No. 75505/1974, Japanese Patent Kokai Publication No. 82358/1982, Japanese Patent Kokai Publication No. 189116/1984 and Japanese Patent Kokoku Publication No. 23381/1983 etc.

However, an excellent prevention effect of coloration cannot be attained by the above methods. In particular, in the case of the aromatic isocyanate compounds which are in solid or semi-molten state at a room temperature, they are usually stored in a solid state at low temperature or in a liquid state by warming. Since they are repeatedly solidified and molten prior to use, they are more liable to color and any satisfactory method for preventing coloration has not been found yet.

When the aromatic isocyanate compounds are reacted with various active hydrogen compounds such as polyols or amines having active hydrogens, reaction controlling agents are often added to the reaction mixture because the reaction rate is so high that the reaction is hardly controllable depending on the kind of the reactant or reaction conditions [for example, cf. U.S. Pat. No. 2,437,867; "Polyurethane Resin", 23 (1969) authored by Keiji Iwata; and HIGH POLYMERS, Vol. XVI, 214 (1962) by J. H. Saunders and K. C. Frisch]. In these cases, however, use of the compounds is extremely limited because coloration becomes worse.

Through an intensive study to solve the above problem, we surprisingly found that an excellent prevention effect of coloration can be obtained by adding a specific organic phosphite ester, 2,6-di-tert.-butyl-4-methylphenol (BHT) and triphenyl phosphite (TPP) thereby completing the present invention.

This invention relates to a method for preventing coloration of an aromatic isocyanate compound, which is characterized in that an organic phosphite ester of formula:

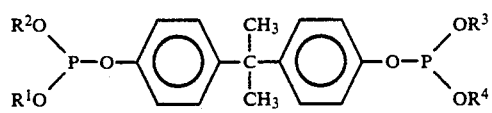

wherein $R^1$, $R^2$, $R^3$ and $R^4$ are, the same or different, each a $C_{4-20}$ hydrocarbon group, BHT and TPP are added to the aromatic isocyanate compound.

The aromatic isocyanate compounds include aromatic diisocyanates such as diphenylmethane diisocyanate (MDI), toluene diisocyanate (TDI) and naphthalene diisocyanate, their urethane or isocyanurate modified compounds and isocyanate prepolymers obtained by reacting with polyols having active hydrogens etc.

Aromatic carboxylic acid chlorides such as benzoyl chloride or isophthalic acid chloride, inorganic acids such as hydrochloric acid or phosphoric acid, aliphatic carboxylic acid such as acetic acid, chloroacetic acid or propionic acid, or their acid anhydrides as reaction controlling agents can be added to the aromatic isocyanate compounds. Addition of benzoyl chloride is preferable.

An addition amount of the reaction controlling agents is usually from 1 to 300 ppm based on the weight of the aromatic isocyanate compound, although it may vary depending on the kind of the aromatic isocyanate compound or active hydrogen compound and the reaction condition. In the case of benzoyl chloride, the amount is usually from 10 to 50 ppm, preferably from 15 to 30 ppm, based on the weight of the aromatic isocyanate compound.

The organic phosphite ester is isopropylidene diphenyl diphosphite wherein $R^1$, $R^2$, $R^3$ and $R^4$ are $C_4$ to $C_{20}$ hydrocarbon groups, preferably alkyl groups such as butyl, hexyl, octyl, tridecyl or stearyl groups or aryl groups such as phenyl, tolyl or xylyl groups. Among them, tetratridecyl-4,4'-isopropylidene diphenyl diphosphite (referred to as tridecyl compound hereinafter) is particularly preferable.

An addition amount of the organic phosphite ester is usually from about 0.005 to about 1.0 parts by weight, preferably from 0.01 to 0.05 parts by weight per 100 parts by weight of the aromatic isocyanate compound, although it may vary depending on the composition and the kind of the aromatic isocyanate compounds. An addition amount of TPP is usually from about 0.005 to about 1.0 parts by weight, preferably from 0.01 to 0.05 parts by weight per 100 parts by weight of the aromatic isocyanate compound. An addition amount of BHT is usually from about 0.005 to about 1.0 parts by weight, preferably from 0.01 to 0.05 parts by weight per 100 parts by weight of the aromatic isocyanate compound.

The present invention is illustrated in detail hereinafter referring to the examples.

EXAMPLE 1

The tridecyl compound, BHT and TPP were added to purified MDI (APHA value of hue: 5) and the mixture was heated to 60° C. and stirred for 1 hour. After charging the mixture in a glass vessel under nitrogen gas atmosphere and sealing the vessel, the mixture was solidified by cooling at 5° C. and stored, thereby subjected to a time-dependent coloration test. APHA values of hue were measured by sampling a quantity of the mixture immediately, 2, 4 and 6 weeds after sealing and then melting the samples at 60° C. Tests by using samples without the addition and the samples with the addition of the tridecyl compound, BHT, TPP, tridecyl compound/BHT, tridecyl compound/TPP and BHT/TPP, respectively, were carried out for comparison. The results are shown in Table 1.

EXAMPLE 2

The test was carried out in the same manner as in Example 1, except that 20 ppm, based on the weight of MDI, of benzoyl chloride (an amount corresponding to an increment of acid value of 5 ppm) was added to purified MDI (APHA value of hue: 5). The results are shown in Table 2.

EXAMPLE 3

The tridecyl compound, BHT and TPP in amounts indicated in Table 3 were added to an isocyanate prepolymer (isocyanate content: 22.9%) obtained by reacting tripropylene glycol with purified MDI (APHA value of hue: 5), and the mixture was heated to 60° C. and mixed for 1 hour with stirring. The mixture was charged in a glass vessel under nitrogen gas atmosphere, the vessel was sealed and the mixture was subjected to a time-dependent coloration test by storing at 45° C. in a thermostatic chamber, APHA values of hue were measured immediately and 4 weeks after sealing. Tests using samples without the addition and with the addition of the tridecyl compound, BHT, TPP, epichlorohydrin, JPP100 (tetraphenyldipropylene glycol diphosphite described in Japanese Patent Kokoku Publication No. 23381/1983), tridecyl compound/BHT, tridecyl compound/TPP and BHT/TPP, respectively, were carried out for comparison. The results are shown in Table 3.

TABLE 1

| Additive | Addition amount (ppm) | Immediately after sealing | 2 weeks after sealing | 4 weeks after sealing | 6 weeks after sealing |
|---|---|---|---|---|---|
| Tridecyl compound/ BHT/TPP | 300/300/ 300 | 5 | 5 | 5 | 10 |
| Non-addition | — | 5 | 200 | 250 | 300 |
| Tridecyl compound | 1000 | 5 | 5 | 20 | 30 |
| BHT | 1000 | 5 | 100 | 120 | 150 |
| TPP | 1000 | 5 | 70 | 90 | 100 |
| Tridecyl compound/ BHT | 500/500 | 5 | 5 | 15 | 25 |
| Tridecyl compound/ TPP | 500/500 | 5 | 5 | 15 | 20 |
| BHT/TPP | 500/500 | 5 | 30 | 50 | 70 |

TABLE 2

| Additive | Addition amount (ppm) | Immediately after sealing | 2 weeks after sealing | 4 weeks after sealing | 6 weeks after sealing |
|---|---|---|---|---|---|
| Tridecyl compound/ BHT/TPP | 300/300/ 300 | 5 | 5 | 10 | 20 |
| Non-addition | — | 5 | 250 | 350 | 400 |
| Tridecyl compound | 1000 | 5 | 10 | 30 | 50 |
| BHT | 1000 | 5 | 150 | 180 | 200 |
| TPP | 1000 | 5 | 100 | 120 | 150 |
| Tridecyl compound/ BHT | 500/500 | 5 | 10 | 30 | 40 |
| Tridecyl compound/ TPP | 500/500 | 5 | 10 | 20 | 40 |
| BHT/TPP | 500/500 | 5 | 50 | 80 | 100 |

TABLE 3

| Additive | Addition amount (ppm) | Immediately after sealing | 4 weeks after sealing |
|---|---|---|---|
| Tridecyl compound/ BHT/TPP | 300/300/300 | 15 | 15 |
| Non-addition | — | 40 | 120 |
| Tridecyl compound | 1000 | 20 | 40 |
| BHT | 1000 | 20 | 80 |
| TPP | 1000 | 20 | 70 |
| Epichlorohydrin | 1000 | 20 | 80 |
| JPP-100 | 1000 | 20 | 50 |
| Tridecyl compound/ BHT | 500/500 | 15 | 25 |
| Tridecyl compound/ TPP | 500/500 | 15 | 20 |
| BHT/TPP | 500/500 | 20 | 50 |

When the organic phosphite ester, BHT and TPP are added to the highly reactive aromatic isocyanate compound such as purified MDI, the original value of hue does not increase during a long period of storage in a solid state at low temperature or in a liquid state by warming, thereby making it possible to obtain an excellent prevention effect of coloration.

Even when the aromatic carboxylic acid chloride such as benzoyl chloride is added as a reaction controlling agent, similar good prevention effect of coloration as in the case where no reaction controlling agent is added can be also obtained.

The aromatic isocyanate compound with adding the organic phosphite ester, BHT and TPP can be widely used as the raw materials for elastomers, foams etc. and as the raw materials for artificial leathers, paints etc.

I claim:

1. A method for preventing coloration of an aromatic isocyanate compound comprising adding to said isocyanate compound:
   i) from 0.005 to 1.0 parts per hundred parts by weight of said isocyanate compound of an organic phosphite ester of the formula:

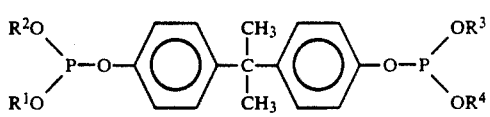

where $R^1$, $R^2$, $R^3$ and $R^4$ are the same or different and represent a $C_4$ to $C_{20}$ hydrocarbon group,
   ii) from 0.005 to 1.0 parts per hundred parts by weight of said isocyanate compound of 2,6-di-tert.-butyl-4-methyl-phenol, and
   iii) from 0.005 to 1.0 parts per hundred parts by weight of said isocyanate compound of triphenylphosphite.

* * * * *